United States Patent [19]

Castellanos et al.

[11] Patent Number: 5,550,265

[45] Date of Patent: Aug. 27, 1996

[54] ONIUM BORATES/BORATES OF ORGANOMETALLIC COMPLEXES AND CATIONIC INITIATION OF POLYMERIZATION THEREWITH

[75] Inventors: Frederic Castellanos, Mulhouse; Jacques Cavezzan, Villeurbanne; Jean-Pierre Fouassier, Morschwiller-le-bas; Christian Priou, Villeurbanne, all of France

[73] Assignee: Rhone-Poulenc Chimie, Courbevoie Cedex, France

[21] Appl. No.: 400,970

[22] Filed: Mar. 8, 1995

Related U.S. Application Data

[62] Division of Ser. No. 35,838, Mar. 23, 1993, Pat. No. 5,468,902.

[30] Foreign Application Priority Data

Mar. 23, 1992 [FR] France .................................. 92 03440

[51] Int. Cl.$^6$ ................................ C07F 5/02; C07F 9/00; C07F 13/00
[52] U.S. Cl. ........................... 556/7; 556/43; 556/46; 556/47; 556/58; 556/143; 556/136
[58] Field of Search ................. 556/7, 43, 46, 556/47, 58, 136, 143

[56] References Cited

U.S. PATENT DOCUMENTS

| | | | |
|---|---|---|---|
| 4,238,619 | 12/1980 | Crivello et al. ............................ | 549/3 |
| 4,992,571 | 2/1991 | Fukuyama et al. ....................... | 556/64 |

FOREIGN PATENT DOCUMENTS

| | | |
|---|---|---|
| 0421659A3 | 4/1991 | European Pat. Off. . |
| 0442635A1 | 8/1991 | European Pat. Off. . |
| 0468651A1 | 1/1992 | European Pat. Off. . |
| 0490269A1 | 6/1992 | European Pat. Off. . |
| 0492282A1 | 7/1992 | European Pat. Off. . |
| WO90/11303 | 10/1990 | WIPO . |
| WO91/14713 | 10/1991 | WIPO . |

OTHER PUBLICATIONS

Xinmin Yang, Charlotte Stern and Tobin J. Marks, Chemical Abstracts, vol. 114, 1991, Columbus, Ohio, Abstract No. 164396g.

Naumann et al., J. J. Chem. Soc., Chem. Commun., 1989, pp. 47–50.

Claudio Pellecchia, Pasquale Longo, Antonio Proto and Adolfo Zambelli, "Novel Aluminoxane–Free Catalysts for Syndiotactic–Specific Polymerization of Styrene", Die Makromolekulare Chemie, Rapid Communications, vol. 13, No. 5, May 1992, pp. 265–268.

Steven R. Bahr and Philip Boudjouk, "Trityl Tetrakis(3, 5–bis(trifluoromethyl)phenyl)–borate: A New Hydride Abstraction Reagent", The Journal of Organic Chemistry, Sep. 25, 1992, vol. 57, No. 20, pp. 5545–5547.

Makromolekulare Chemie, Rapid Commun. vol. 12, 1991, pp. 663–667, Pellecchia.

Chemical Abstracts, vol. 113, Columbus, Ohio, Fujui, abstract No. 32008b.

Journal of the Am. Chemical Society, vol. 113, 1991, pp. 8570–8571, Chien et al.

Journal of the Am. Chemical Society, vol. 113, 1991, pp. 7823–7825, Zou et al.

Journal of Organometallic Chemistry, vol. 2, 1964, pp. 245–250, Massey et al.

*Primary Examiner*—Porfirio Nazario-Gonzales
*Attorney, Agent, or Firm*—Burns, Doane, Swecker & Mathis, L.L.P.

[57] ABSTRACT

Novel onium borates of an element of Groups 15 to 17 of the Periodic Table, or borates of an organometallic complex of an element of Groups 4 to 10 of the Periodic Table, well suited for the photochemical/electron beam cationic initiation of polymerization/crosslinking, the anionic borate moiety of which having the formula:

$$[BX_aR_b]^-$$

which a and b are integers ranging from 0 to 4 and a+b=4; the symbols X are each a halogen atom when ranges up to 3 and an OH functional group when a ranges up to 2; and the symbols R, which may be identical or different, are each a phenyl radical substituted by at least one element or electron-withdrawing substituent or by at least two halogen atoms, or an aryl radical containing at least two aromatic ring members, or such aryl radical bearing at least one electron-withdrawing substituent.

3 Claims, No Drawings

ONIUM BORATES/BORATES OF ORGANOMETALLIC COMPLEXES AND CATIONIC INITIATION OF POLYMERIZATION THEREWITH

This application is a divisional of application Ser. No. 08/035,838, filed Mar. 23, 1993, now U.S. Pat. No. 5,468,902.

BACKGROUND OF THE INVENTION

1. Field of the Invention

The present invention relates to novel onium borates or borates of organometallic complexes which are cationic initiators of polymerization, to a process for the preparation thereof and to the use of such novel borates for the polymerization or crosslinking of functional polymers or monomers by photochemical activation, or activation under an electron beam.

2. Description of the Prior Art

Onium salts or salts of organometallic complexes are well known to this art as initiators of the cationic polymerization of monomers or of polymers substituted by functional groups of the epoxy or vinyl ether type, or the like (U.S. Pat. Nos. 4,069,054; 4,450,360; 4,576,999 and 4,640,967; Canadian Patent No. 1,274,646; European Application EP-A-203,829).

It has been observed that the best results are obtained when the anion of the initiator salt is $SbF_6^-$; the initiator salts containing this type of anion, however, present toxicity risks.

It is also known to this art to use ferrocenium perfluorotetraphenylborates of the bis($\eta^5$-cyclopentadienyl)Fe$^+$ tetrakis(pentafluorophenyl)borate type for generating catalysts of the Ziegler-Natta variety, which catalysts are then used for polymerizing vinyl monomers (EP-A-481,480; EP-A-468,651; EP-A418,044; EP-A-468,537; EP-A-421,659 and EP-A-277,044; Makromol. Chem., Rapid Commun., 12, 663–667 (1991); Organometallics, 10, 840–842 (1991); it has been observed that the ferrocenium perfluorotetraphenylborates of the bis($\eta^5$-cyclopentadienyl) Fe$^+$ tetrakis (pentafluorophenyl) borate type are not photoinitiators.

SUMMARY OF THE INVENTION

Novel such photoinitiator salts have now been found containing an anion with a nucleophilicity close to that of $SbF_6^-$ but which does not present the disadvantages thereof.

Briefly, the present invention features onium borates of an element from Groups 15 to 17 of the Periodic Table [Chem. & Eng. News, vol. 63, No. 5, 26; 4 February 1985] or borates of an organometallic complex of an element from Groups 4 to 10 of the Periodic Table (same reference), the cationic moiety of which comprising:

(1) an onium salt having the formula (I):

$$[(R^1)_n\text{—}A\text{—}(R^2)_m]^+ \quad (I)$$

in which A is an element from Groups 15 to 17 of the Periodic Table, such as I, S, Se, P, N and the like; $R^1$ is a $C_6$–$C_{20}$ heterocyclic or carbocyclic aryl radical, said heterocyclic radical containing at least one of the heteroatoms, nitrogen, sulfur, and the like; $R^2$ is $R^1$ or a linear or branched, $C_1$–$C_{30}$ alkenyl or alkyl radical, said radicals $R^1$ and $R^2$ optionally being substituted by a $C_1$–$C_{25}$ alkoxy, $C_1$–$C_{25}$ alkyl, nitro, chloro, bromo, cyano, carboxyl, ester, mercapto group and the like; n is an integer ranging from 1 to v+1, with y being the valence of the element A; and m is an integer ranging from 0 to v–1 with n+m=v+1;

(2) an oxoisothiochromanium salt as described in WO-A-90/11,303, especially the 2-ethyl-4-oxoisothiochromanium or 2-dodecyl-4-oxoisothiochromanium sulfonium salt; or (3) an organometallic salt having the formula (II):

$$(L^1L^2L^3M)^{1+} \quad (II)$$

in which M is a metal from Groups 4 to 10 of the Periodic Table, especially iron, manganese, chromium, cobalt, and the like; $L^1$ is one ligand joined to the metal M via $\pi$ electrons, said ligand being selected from among the $\eta^3$-alkyl, $\eta^5$-cyclopentadienyl and $\eta^7$-cycloheptatrienyl ligands and the $\eta^6$-aromatic compounds selected from among the optionally substituted $\eta^6$-benzene ligands and the compounds having from 2 to 4 condensed rings, each ring being capable of contributing to the valence shell of the metal M via 3 to 8 $\eta$ electrons; $L^2$ is one ligand joined to the metal M via $\eta$ electrons, said ligand being selected from among the $\eta^7$-cycloheptatrienyl ligands and the $\eta^6$-aromatic compounds selected from among the optionally substituted $\eta^6$-benzene ligands and the compounds having from 2 to 4 condensed rings, each ring being capable of contributing to the valence shell of the metal M via 6 or 7 $\eta$ electrons; $L^3$ is from 0 to 3 identical or different ligands joined to the metal M via $\sigma$ electrons, said ligand(s) being selected from among CO and $NO_2^+$, with the proviso that the total electron charge q of the complex to which $L^1$, $L^2$ and $L^3$ contribute and the ionic charge of the metal M are positive and equal to 1 or 2; and the anionic borate moiety of which having the formula:

$$[BX_aR_b]^-$$

in which a and b are integers ranging from 0 to 4 with a+b=4; each X is a halogen atom (chlorine or fluorine) with a=0 to 3, an OH functional group with a=0 to 2; the symbols R, which may be identical or different, are each a phenyl radical substituted by at least one electron-withdrawing group, such as $CF_3$, $NO_2$, CN and the like, or by at least two halogen atoms (most particularly fluorine), with the proviso that the cationic moiety is an onium of an element from Groups 15 to 17 of the Periodic Table; or are each a phenyl radical substituted by at least one element or one electron-withdrawing group, especially a halogen atom (most particularly fluorine), $CF_3$, $NO_2$, CN and the like, with the proviso that the cationic moiety is an organometallic complex of an element from Groups 4 to 10 of the Periodic Table; or are each an aryl radical containing at least two aromatic ring members, such as biphenyl, napthyl and the like, optionally substituted by at least one element or one electron-withdrawing group, especially a halogen atom (most particularly fluorine), $CF_3$, $NO_2$, CN and the like, whatever the cationic moiety.

DETAILED DESCRIPTION OF PREFERRED EMBODIMENTS OF THE INVENTION

More particularly according to the present invention, exemplary borate anions include:

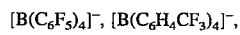

$[B(C_6F_5)_4]^-$, $[B(C_6H_4CF_3)_4]^-$,

The onium salts of formula (I) are described in the literature, patent and otherwise, and especially in U.S. Pat. Nos. 4,026,705; 4,032,673; 4,069,056; 4,136,102 and 4,173,476, for example.

The following cations, wherein Φ is phenyl, are very particularly representative:

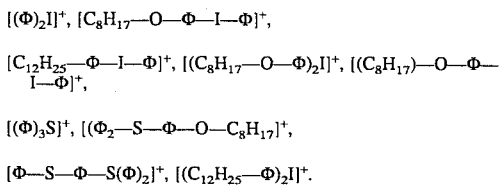

The organometallic salts of formula (II) appear among those described in U.S. Pat. Nos. 4,973,722 and 4,992,572 and the European Patent Applications
EP-A-203,829, EP-A-323,584 and EP-A-354,181.

Exemplary of such organometallic salts, very particularly representative are:

($\eta^5$-Cyclopentadienyl) ($\eta^6$-toluene)Fe$^+$,
($\eta^5$-Cyclopentadienyl) ($\eta^6$-1-methylnaphthalene) Fe$^+$,
($\eta^5$-Cyclopentadienyl) ($\eta^6$-cumene) Fe$^+$,
Bis($\eta^6$-mesithylene)Fe$^+$,
Bis ($\eta^6$-benzene)Cr$^+$.

Thus, exemplary initiators of the invention include:

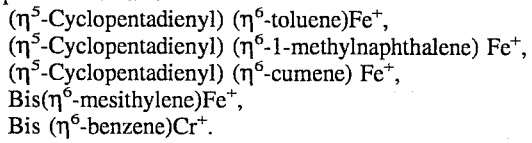

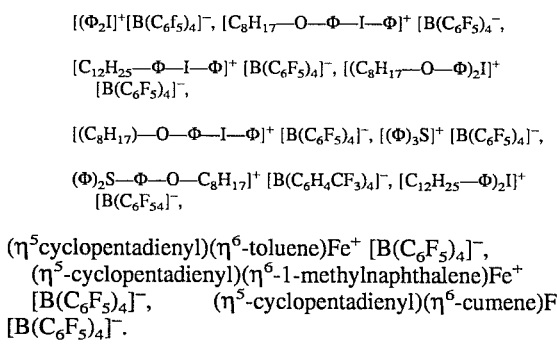

The initiator salts of the present invention can be prepared by an exhange reaction between a salt of the cationic moiety (halide such as chloride, iodide and the like, hexafluorophosphate, tetrafluoroborate, tosylate and the like) and an alkali metal salt (sodium, lithium or potassium) of the anionic moiety.

The operating conditions (respective amounts of reactants, choice of solvents, duration, temperature, stirring and the like) are easily determined by one skilled in this art; they must permit recovery of the desired initiator salt in the solid state, by filtration of the precipitate formed, or in the oily state by extraction using a suitable solvent.

The alkali metal salts of the anionic moiety can be prepared in known manner, by an exchange reaction between a haloborated compound and an organometallic compound (of magnesium, lithium, tin and the like) bearing the desired hydrocarbon groups, in a stoichiometric amount, optionally followed by a hydrolysis using an aqueous solution of alkali metal halide; this type of synthesis is, for example, described in *J. of Organometallic Chemistry*, Vol. 178, p. 1–4, (1979); *J.A.C.S.*, 82, 5298 (1960); *Anal. Chem. Acta*, 44, 175–183 (1969); U.S. Pat. No. 4,139,681 and DE-A-2,901,367; *Zh. Org. Khim.*, Vol. 25, No. 5—pages 1099–1102, (May 1989).

The preparation of the salts of the cationic moiety of formula (II) is described, especially, in D. Astruc, *Tetrahedron Letters*, 36, p. 3437 (1973); D. Astruc, *Bull. Soc. Chim. Fr.*, 1–2, p. 228 (1976); D. Astruc, *Bull. Soc. Chim. Fr.*, 11–12, p. 2571 (1975); D. Astruc, *CR Acad. Sc., Paris*, series C, 272, p. 1337 (1971); A. N. Nesmeyanov et al, *Izves. Akad. Nauk SSSR*, ser. Khim., 7, P. 1524 (1969); A. N. Nesmeyanov et al., *Dokl. Akad. Nauk SSSR*, 160(6), p. 1327 (1965); A. N. Nesmeyanov et a., *Dokl. Akad. Nauk SSSR*, 149(3), p. 615 (1963).

The initiator salts of the present invention are useful for polymerizing or crosslinking, by photochemical activation (especially under ultraviolet radiation) or under an electron beam, monomers or polymers bearing functional groups such as epoxy groups, vinyl ether groups, and the like. The borates of the organometallic complexes can additionally be used as thermal polymerization initiators.

In order to further illustrate the present invention and the advantages thereof, the following specific examples are given, it being understood that some are intended only as illustrative and in nowise limitative.

EXAMPLE 1

Diphenyliodonium tetrakis (pentafluorophenyl)borate $[(\Phi_2I)^+ [B(C_6F_5)_4]^-$ Preparation of lithium tetrakis(tetrafluorophenyl)-borate:

A 4,000 ml, four-necked, round-bottom flask, equipped with a mechanical stirrer, a water-cooled reflux condenser, a thermometer and a dropping funnel, was employed. The assembly was dried beforehand under an argon atmosphere.

1,600 ml of anhydrous pentane and 126.8 g (or 0.513 mol) of bromopentafluorobenzene were charged therein. This medium was stirred and then cooled to −78° C. using a solid carbon dioxide/acetone bath.

313 ml of a 1.6M solution of n-butyllithium in hexane were charged into the dropping funnel and were then added dropwise over 50 minutes.

The mixture was maintained under stirring for 5 hours at a temperature of −78° C.

125 ml of a 1M solution of boron trichloride in hexane were charged into the dropping funnel and added to the mixture over thirty minutes. The cooling bath was removed and the reaction mixture was permitted to return to room temperature. It was then maintained under stirring for 12 hours. The reaction mixture was hydrolyzed by slow addition of 625 ml of water. The two phases were separated and the organic phase was washed with two 125 ml fractions of water. The aqueous phases were combined and were then extracted three times with ether (3×125 ml). The ether phases were combined and dried over magnesium sulfate. The ether was evaporated under reduced pressure and 101 g (or a yield of 99%) of lithium tetrakis(pentafluorophenyl)borate were recovered.

Preparation of diphenyliodonium tetrakis(pentafluorophenyl)borate:

7.17 g (or 22.6 mmol) of diphenyliodonium chloride were dissolved in 300 ml of water in a 1,000 ml Erlenmeyer flask. 15.52 g (or 22.6 mmol) of lithium tetrakis(pentafluorophenyl)borate in solution in 250 ml of water were added dropwise. The mixture was maintained under stirring for 30 minutes and was then filtered. The filtrate was dried under reduced pressure (133 Pa) overnight with the exclusion of light. 16.33 g (or a yield of 75%) of diphenyliodonium tetrakis(pentafluorophenyl)borate were thus recovered.

EXAMPLE 2

(4-Octyloxyphenyl)phenyliodonium tetrakis (pentafluorophenyl)borate
$[(C_8H_{17})-O-\Phi-I-\Phi]^+ [B(C_6F_5)_4]^-$ Preparation of octyl phenyl ether 44.8 g (or 0,477 mol) of phenol, 38.6 g (or 0.2 mol) of n-bromooctane, 6 g of tetrabutylammonium bromide, 26.8 g of potassium hydroxide, 100 ml of water and 100 ml of toluene were charged into a 500 ml, three-necked, round-bottom flask equipped with a mechanical stirrer, a thermometer and water-cooled reflux condenser. This medium was stirred and was then heated to reflux for 20 hours. The reaction mixture was then cooled to room temperature. The phases were settled and separated. The organic phase was washed with 100 ml of a 0.5N sodium hydroxide solution and then with five 100 ml fractions of water. It was then dried over magnesium sulfate and the solvent was then driven off under reduced pressure at a temperature of 85° C.

41.5 g (or a yield of 95%) of n-octyl phenyl ether, which could be used subsequently without additional purification, were recovered.

Preparation of hydroxytosyloryiodobenzene 80.53 g (or 0.25 mol) of iodobenzene diacetate, 300 ml of water and 100 ml of acetic acid were charged into a 1,000 ml, round-bottom flask equipped with a mechanical stirrer, a water-cooled reflux condenser and a dropping funnel. This medium was stirred and heated to 40° C. 47.55 g (or 0.25 mol) of paratoluenesulfonic acid monohydrate were then added over five minutes via the dropping funnel. The reaction mixture was maintained at 40° C. for two hours and was then cooled to 25° C. A white precipitate appeared. It was recovered by filtration and then dried under reduced pressure.

68.15 g (or a yield of 70%) of the desired product were obtained.

Preparation of (4-octyloxyphenyl)-phenyliodonium tosylate:

22.2 g (or 0.057 mol) of hydroxytosyloxyiodobenzene, 9 g (or 0.04 mol) of n-octyl phenyl ether, 5 ml of acetonitrile and 1.5 ml of acetic acid were charged into a 250 ml Erlenmeyer flask equipped with a magnetic stirrer bar. This mixture was stirred and was heated to a temperature of 40° C. for 2 hours, 30 minutes. 1.5 ml of glacial acetic acid was then added and the mixture was then maintained for 5 hours at 40° C. The reaction mixture was permitted to cool and 150 ml of water were added while stirring vigorously. This mixture was then stirred for 12 hours at room temperature and was then separated. The organic phase was washed several times with water, until a yellow precipitate appeared. This solid was recovered by filtration, was washed with 50 ml of ether and was then dried under vacuum at a temperature of 45° C.

19.5 g ( or a yield of 76% ) of ( 4octyloxyphenyl)phenyliodonium tosylate were thus recovered.

Preparation of (4-octyloxyphenyl)-phenyliodonium tetrakis(pentafluorophenyl)borate:

5 g (or 0.0086 mol) of (4-octyloxyphenyl)phenyliodonium tosylate were dissolved in 350 ml of acetone in a 500 ml Erlenmeyer flask equipped with a magnetic stirrer bar. While light was excluded, 3.4 g (or 0.0103 mol) of lithium tetrakis(pentafluorophenyl)borate in solution in 50 ml of acetone were added. The mixture was stirred for 48 hours and was then filtered to remove the lithium p-toluenesulfonate formed. The acetone was evaporated under reduced pressure and 7.98 g (or a yield of 92%) of ((4-octyloxyphenyl)phenyliodonium tetrakis(pentafluorophenyl)borate were recovered.

EXAMPLE 3

Bis (dodecylphenyl) iodonium tetrakis (pentafluorophenyl)borate $[(C_{12}H_{25}-\Phi)_2I]^+$ $[B(C_6F_5)_4]^-$ Preparation of bis(dodecylfluorophenyl)iodonium chloride:

100 g (or 0.405 mol) of dodecylbenzene, 43.5 g (or 0,203 mol) of potassium iodate, 199.6 g of acetic acid and 59.5 g of acetic anhydride were charged into a 1,000 ml, round-bottom flask equipped with a mechanical stirrer, a water-cooled reflux condenser and a dropping funnel. The mixture was stirred and then cooled in an ice bath to 0° C. A mixture of 59.8 g of sulfuric acid and 39.86 g of acetic acid was charged into the dropping funnel. This mixture was added to the reaction mixture over 25 minutes. The reaction mixture was maintained under stirring for 18 hours at room temperature. 750 ml of water were then added and the reaction mixture was then extracted with three ether fractions (3×350 mol). The ether phases were combined and then evaporated under reduced pressure. The concentrate was taken up in 540 ml of a saturated sodium chloride solution, and the mixture was then cooled in an ice bath for two hours. The product was recovered by filtration on sintered glass No. 4. The solid was then recrystallized twice from acetone. 69.18 g (or a yield of 52%) of bis(dodecylphenyl)iodonium chloride were recovered by filtration.

Preparation of bis(dodecylphenyl)iodonium tetrakis(pentafluorophenyl)borate:

3.76 g of bis(dodecylphenyl)iodonium chloride were dissolved in 500 ml of acetone in a 1,000 ml Erlenmeyer flask. A solution of 5 g of lithium tetrakis(pentafluorophenyl)borate in 100 ml of acetone was then added dropwise. The mixture was maintained under stirring for two days, with the exclusion of light, and the sodium chloride formed was then removed by filtration. 8 g (or a yield of 90%) of bis(dodecylphenyl)iodonium tetrakis(pentafluorophenyl)borate were recovered after evaporation of the acetone.

EXAMPLE 4

$(\eta^5$-Cyclopentadienyl$)(\eta^6$-cumene$)$Fe$^+$ tetrakis(pentafluorophenyl)borate 4 g (or 0.0215 mol) of ferrocene, 7.64 g of aluminum chloride, 0.11 g of aluminum powder and 27 g of cumene were charged into a 250 ml, three-necked, round-bottom flask equipped with a mechanical stirrer, a water-cooled reflux condenser, a thermometer and a dropping funnel.

This medium was stirred and placed under an inert nitrogen atmosphere. The reaction mixture was heated over 2 hours, and then 4.04 g of titanium chloride were added dropwise. This medium was heated for 1 hour at 100° C. and the mixture was then permitted to return gradually to room temperature. The reaction mixture was poured into a mixture of 30 g of ice and 8 g of 37.5% HCl. The mixture was maintained under stirring for 30 min and 0.7 g of hydrogen peroxide was then added. This mixture was maintained under stirring for 30 min and was then filtered on a sintered glass No. 4. The liquid fraction was recovered; after settling and separation of the phases, a solution of 15.4 g of potassium tetrakis(pentafluorophenyl)borate in 800 ml of water was introduced into the aqueous phase. This mixture was maintained under stirring for 2 hours.

The precipitate was separated by filtration and was then dried under vacuum; 14.3 g (or a yield of 73%) of the desired product were obtained.

EXAMPLE 5 ($\eta^5$-Cyclopentadienyl) ($\eta^6$-toluene) Fe$^+$ tetrakis (pentafluorophenyl)borate 50 ml of an aqueous solution containing 3.58 g of ($\eta^5$-cyclopentadienyl)($\eta^6$-toluene)Fe$^+$ hexafluorophosphate were added to a 250 ml, three-necked, round-bottom flask containing 7 g of sodium tetrakis(pentafluorophenyl)borate dissolved in 100 ml of distilled water. The mixture was subjected for 1 hour to magnetic stirring. A clear precipitate formed which was separated by filtration and then dried under vacuum for 24 hours. 8.5 g (or a yield of 95%) of ($\eta^5$-cyclopentadienyl) ($\eta^6$-toluene)Fe$^+$ tetrakis(pentafluorophenyl)borate were thus obtained.

The formula of the product obtained was confirmed by $^1$H and $^{19}$F NMR and by mass spectrometry.

EXAMPLE 6 ($\eta^5$-Cyclopentadienyl) ($\eta^6$-1-methylnaphthalene) Fe$^+$ tetrakis(pentafluorophenyl)borate The preparation was carried out as in Example 4, from 7 g of sodium tetrakis(pentafluorophenyl)borate and from 3.5 g of ($\eta^5$-cyclopentadienyl)($\eta^6$-1-methylnaphthalene)Fe$^{30}$ tetrafluoroborate; 8.9 g of the expected product were obtained.

The formula was confirmed by NMR analysis and by mass spectrometry.

EXAMPLE 7

Photocrosslinking of an epoxidized monomer to form a thin layer

A bath was prepared according to the following procedure:

(i) 2 parts by weight of photoinitiator A in a 50% by weight solution in methanol were added, to (ii) 100 parts by weight of epoxidized monomer UVR-6110® (3,4-epoxycyclohexylmethyl 3,4-epoxycyclohexanecarboxylate marketed by Union Carbide).

The mixture was maintained at room temperature for 30 minutes with mechanical stirring.

The mixture was then deposited (approximately 2 to 3 g/m$^2$) on glassine paper (Sibille® 9530 marketed by Sibille) using a Mayer® No. 0 bar (marketed by Erichsen G-B).

The coated paper was passed under a U.V. lamp of the Fusion System® F 450 type (marketed by Fusion) and characterized by:

(a) a wavelength of 360 mm,
(b) an absence of electrodes,
(c) excitation by microwaves,
(d) a power of 120 W per cm irradiated.

The irradiation energy, measured with a Uvicure® cell from Eit-USA, was 0.025 J.cm$^{-2}$ after one pass under the UV lamp at a speed of 33 m/min.

The winding speed in m/min necessary for curing the layer was recorded.

The number of passages as well as the winding speeds of the paper appear in the following Table; the performance of the initiator prepared in Example 1 is compared with that of an initiator which had an equivalent cation but the anion on which was selected from those of the prior art.

It was observed that with an equivalent cation:

(1) the anion B(C$_6$F$_5$)$_4^-$ was as effective as the anion SbF$_6^-$ without exhibiting the toxicity problems of the latter;

(2) the anion B(C$_6$F$_5$)$_4^-$ was much more active than the anions AsF$_6^-$, PF$_6^-$ and BF$_4^-$;

(3) the anions B(C$_6$F$_5$)$_4^-$ and B(C$_6$H$_4$F)$_4^-$ were ineffective in crosslinking the epoxidized monomer to form a thin layer.

| Photoinitiator A | Number of Passages | Winding speed in m/min |
|---|---|---|
| (Φ)$_2$I$^+$B(C$_6$F$_5$)$_4^-$ | 1 | 60 |
| (Φ)$_2$I$^+$SbF$_6^-$ | 1 | 60 |
| (Φ)$_2$I$^+$AsF$_6^-$ | 3 | 20 |
| (Φ)$_2$I$^+$PF$_6^-$ | 4 | 15 |
| (Φ)$_2$I$^+$BF$_4^-$ | 10 | 6 |
| (Φ)$_2$I$^+$B(C$_6$H$_5$)$_4^-$ | not crosslinked | 0 |
| (Φ)$_2$I$^+$B(C$_6$H$_4$F)$_4^-$ | not crosslinked | 0 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An onium borate, the cationic moiety of which having the formula (II):

$$(L^1L^2L^3M)^{q+} \qquad (II)$$

in which M is a metal of Groups 4 to 10 of the Periodic Table; L$^1$ is a ligand associated with the metal M via $\eta$ electrons and is an $\eta^3$-alkyl, $\eta^5$-cyclopentadienyl or $\eta^7$-cycloheptatrienyl ligand or an $\eta^6$-aromatic compound selected from among the optionally substituted $\eta^6$-benzene ligands and compounds having from 2 to 4 condensed ring members, each ring member contributing to the valence shell of the metal M via 3 to 8 $\rho$ electrons; L$^2$ is a ligand associated with the metal M via $\rho$ electrons and is an $\eta^7$-cycloheptatrienyl ligand or an $\eta^6$-aromatic compound selected from among the optionally substituted $\eta^6$-benzene ligands and compounds having from 2 to 4 condensed ring members, each ring member contributing to the valence shell of the metal M via 6 or 7 $\pi$ electrons; and L$^3$ represents from 0 to 3 identical or different ligands associated with the metal M via $\sigma$ electrons and is CO or NO$_2^+$ ligands, the total electron charge q of the complex to which L$^1$, L$^2$ and L$^3$ contribute and the ionic charge of the metal M being positive and equal to 1 or 2; and the anionic borate moiety of which having the formula:

$[BX_aR_b]^-$ in which a and b are integers ranging from 0 to 4 and a+b=4; the symbols X are each a halogen atom when a ranges up to 3 and an OH functional group when a ranges up to 2; and the symbols R, which may be identical or different, are each a phenyl radical substituted by at least one element or electron-withdrawing substituent.

2. The onium borate as defined by claim 1, said cationic moiety of which having one of the formulae: ($\eta^5$-cyclopentadienyl) ($\eta^6$-1-methylnaphthalene) $Fe^+$, ($\eta^5$-cyclopentadienyl) ($\eta^6$-cumene) $Fe^+$, bis($\eta^6$-mesithylene)$Fe^+$ or bis ($\eta^6$-benzene) $Cr^+$.

3. The onium borate as defined by claim 1, wherein said onium borate is ($\eta^5$-cyclopentadienyl) ($\eta^6$-toluene) $Fe^+$ [B$(C_6F_5)_4$]$^-$, ($\eta^5$-cyclopentadienyl) ($\eta^6$-1-methylnaphthalene) $Fe^+$ [B $(C_6F_5)_4$]$^-$, or ($\eta^5$-cyclopentadienyl) ($\eta^6$-cumene) $Fe^+$ [B $(C_6F_5)_4$].

\* \* \* \* \*